United States Patent [19]
Makino et al.

[11] Patent Number: 5,090,799
[45] Date of Patent: Feb. 25, 1992

[54] OPHTHALMOLOGICAL MEASUREMENT METHOD AND APPARATUS

[75] Inventors: Misao Makino, Hachiouji; Kiyoshi Hashimoto; Toshiaki Sugita, both of Hino, all of Japan

[73] Assignee: Kowa Company Ltd., Japan

[21] Appl. No.: 507,390

[22] Filed: Apr. 9, 1990

[30] Foreign Application Priority Data

Apr. 10, 1989 [JP] Japan .................................. 1-87857
Apr. 12, 1989 [JP] Japan .................................. 1-90788

[51] Int. Cl.⁵ .............................................. A61B 3/10
[52] U.S. Cl. .................................... 351/221; 128/691
[58] Field of Search ............... 351/206, 221, 243, 205, 351/246; 606/4, 5, 6; 128/691

[56] References Cited

U.S. PATENT DOCUMENTS 4,950,070 8/1990 Aizu et al. ..................... 351/221
4,952,050 8/1990 Aizu et al. ..................... 351/221

Primary Examiner—Paul M. Dzierzynski
Attorney, Agent, or Firm—Bruce L. Adams; Van C. Wilks

[57] ABSTRACT

In an ophthalmological measurement method and apparatus, a laser beam of predetermined diameter is projected to the eye fundus and movement of a speckle pattern formed by light scattered by blood cells in blood vessel is detected by a photosensor as fluctuation in speckle light intensity to produce a speckle signal. The speckle light intensity will fluctuate more rapidly with a smaller output from the photosensor when cell velocities are high, while a low cell travel speed will decrease the lowering of the output therefrom. The speckle signal is integrated to produce an integrated speckle signal which is evaluated in terms of a rate of change to discriminate edges of a blood vessel. The integrated speckle signal is used to identify the blood vessel for automatic tracking of the blood vessel or for measurement of its diameter.

18 Claims, 6 Drawing Sheets

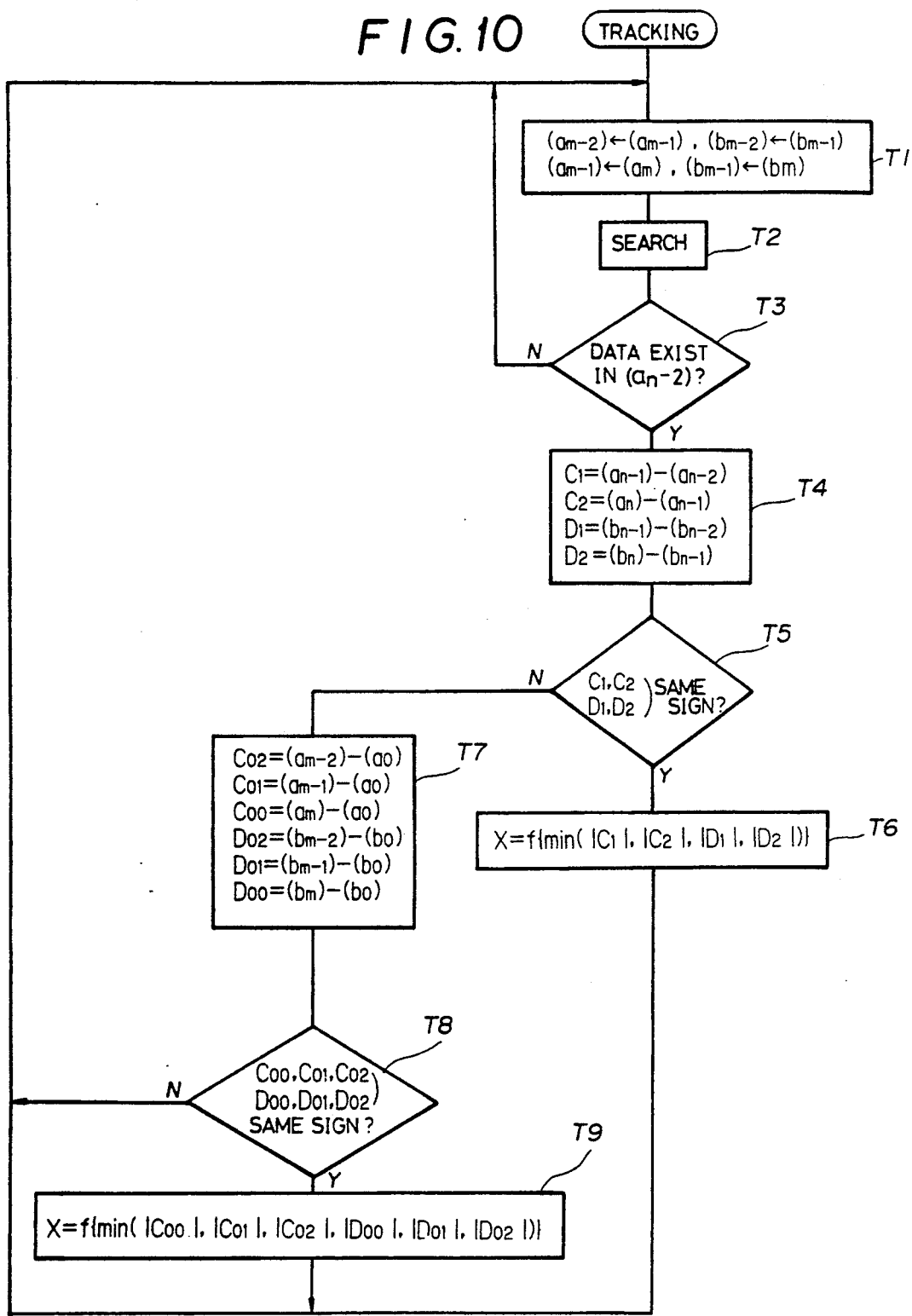

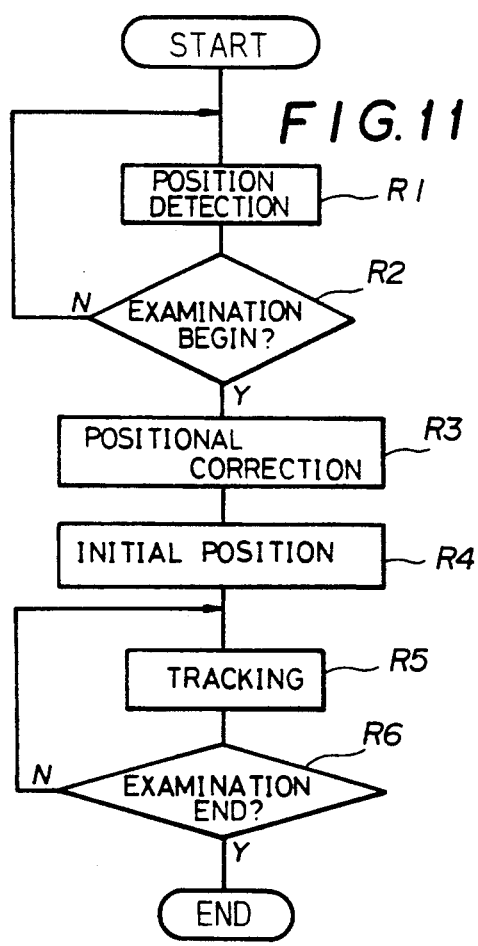
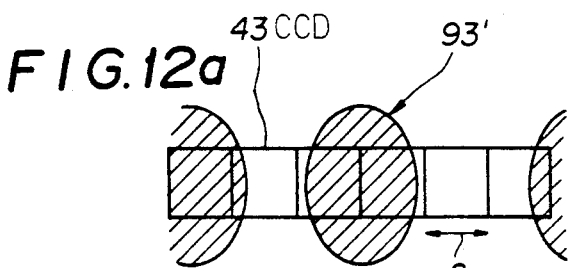
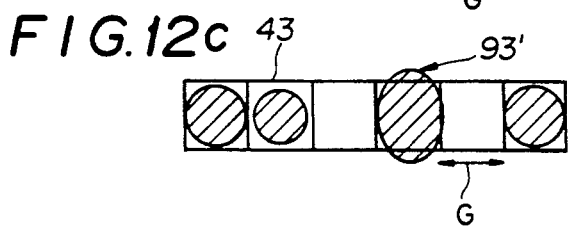
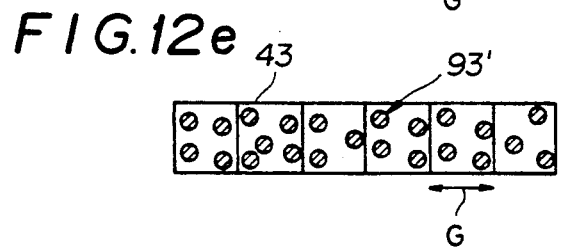
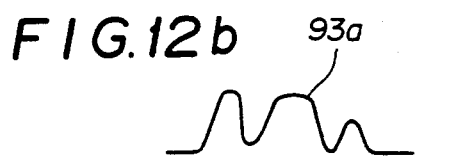
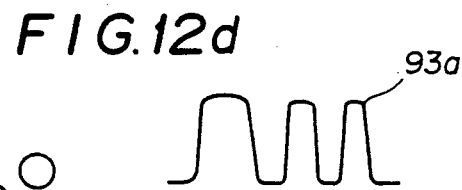
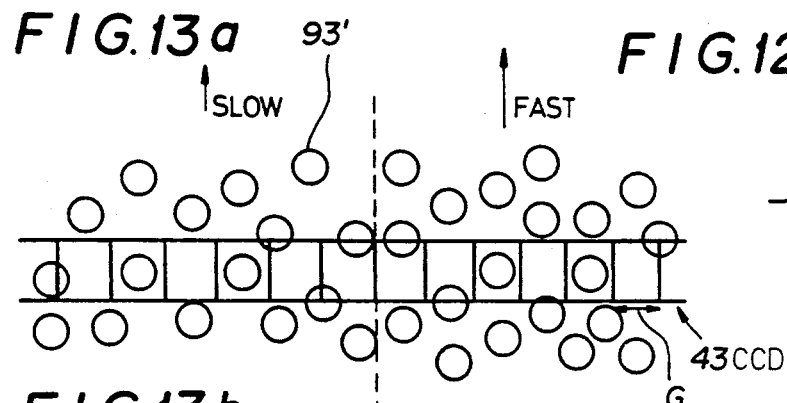
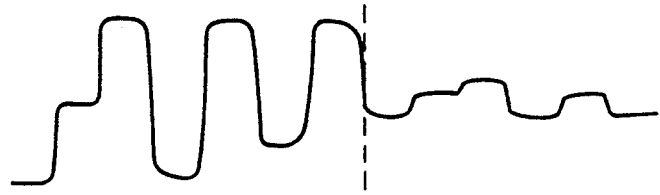

OPHTHALMOLOGICAL MEASUREMENT METHOD AND APPARATUS

BACKGROUND OF THE INVENTION

1. Field of the Invention

This invention relates to an ophthalmological measurement method and apparatus, and more particularly to an ophthalmological measurement method and apparatus in which the eye fundus is illuminated by a laser beam having a predetermined diameter and the motion of a laser speckle pattern formed by laser light scattered and reflected from the eye fundus is detected at an observation point as fluctuations in the speckle light intensity to produce a speckle signal which is evaluated

2. Description of the Prior Art

Various conventional methods are used for ophthalmological measurement comprising illuminating the eye fundus with a laser beam, detecting the light scattered by the eye fundus and analyzing and evaluating this light. There are, for example, laser Doppler methods for measuring blood flow in retinal and other tissue described in "Investigative Ophthalmology," vol. 11 No. 11, page 936 (November 1972) and "Science," vol.186 (November 1974) page 830, and in Japanese Unexamined Patent Publication Nos. 55-75668, 55-75669, 55-75670, 52-142885 (corresponding to GB 13132/76 and U.S. Pat. No. 4,166,695), 56-125033 (corresponding to GB 79/37799), 58-118730 (corresponding to U.S. Pat No. 4,402,601) and U.S. Pat. No. 4,142,796. However, these laser Doppler methods involve the use of a high precision optical system, are complicated to use and provide results which lack repeatability and reliability, all of which make practical application difficult.

It is, on the other hand, known that when a laser beam strikes an object which causes diffusion or scattering of the beam, the light scattering from the object gives rise to a speckle pattern caused by interference between reflected rays of the coherent light. The laser speckle method utilizes this to evaluate the state of tissues in the eye fundus. There are, for example, the methods described in Japanese Unexamined Patent Publication Nos. 62-275431 (U.S. Pat. No. 4,734,107 and EPC 234869), 63-238843 (EPC 284248) and 63-242220 (EPC 285314).

These publications describe the use of a detecting aperture to extract time-base fluctuations in the intensity of speckles formed at an optical Fourier Transform plane with respect to the eye fundus, or at the Fraunofer refraction plane, or at an image plane (or a magnified image plane) that is conjugate with respect to the eye fundus, and the blood flow state is determined by an evaluation of the speckle signal thus obtained.

A major obstacle to the clinical application of the above systems has been their susceptibility to the effects of movements, such as movement of the subject's eye, vibration and the like. This frequently causes unwanted movement of speckle patterns on the detection plane, thus throwing the detecting aperture and laser beam out of alignment during measurement. One way to overcome this is described in the laser-Doppler method of Japanese Patent Publication No. 56-125033. This involves the mechanical scanning of the eye fundus image on the detection plane and using differences between the light reflectance of the walls of a blood vessel and that of other areas of tissue to distinguish blood vessels, and correcting for positional deviation. A drawback of this method is that it requires a mechanism for the mechanical scanning of the eye fundus image, which makes the apparatus too large and complex to be practical.

Another method, described in Applied Optics, Vol. 27, No. 6, page 1113 (Mar. 15, 1988) and in Japanese Patent Publication No. 63-288133 (U.S. Pat No. 014994), shows the feasibility of an image scanning arrangement which allows blood vessels to be distinguished and tracked automatically. However, the method is based on the wavelength dependency of reflected light and relies for its implementation on a plurality of laser beams of different wavelengths which are projected in sequence. Again, this makes the apparatus complex, impractical and costly. A further drawback is that when corneal reflection is used to detect eye movement, the detection precision is not high enough for the purposes of correcting for movement by the blood vessel.

Conventional tracking methods involving the detection of eye movement include one in which the corneal surface is illuminated by a laser beam and movement of the reflected light is used to detect and track such eye movement, while another method uses differences between two images of the eye fundus obtained by a TV camera or other such imaging means.

However, such methods involve detection of eye surface movement and are only able to provide a low level of intraocular tracking precision. Moreover, eye fundus images obtained via a TV camera usually suffer from a poor S/N ratio owing to the amount of light being insufficient for the task, and the apparatus required to detect movement based on differences between two images is large and complex.

On the other hand, the speckle pattern moves as the scattering object moves, so that it is proposed to detect its movement as a fluctuation in the light intensity at the observation point to obtain the difference of the traveling speed of the object depending on the signal intensity.

To discriminate the blood vessel parts and measure the diameter of the blood vessel, there has been proposed a method in which the eye fundus is photographed using a fundus camera to measure the diameter of the blood vessel on the basis of the photographed eye fundus or a method in which a television camera is used to take a picture of the eye fundus and the eye fundus image is subjected to an image processing (for example, image sampling, A/D converting, sharpening, masking, filtering) to determine the diameter of the blood vessel.

Such conventional methods need a long time to obtain measurement results because the eye fundus must be photographed, thus making it impossible to measure the diameter of the blood vessel on real time. On the other hand, the eye fundus image taken by the television camera is usually underexposed with a poor S/N ratio. This necessitates a complicated image processing and results in a bulky and expensive apparatus.

SUMMARY OF THE INVENTION

It is therefore an object of the invention to provided an improved ophthalmological measurement method and apparatus employing the laser speckle phenomenon which is simple and straightforward in construction and is able to detect eye movement and automatically track the movement in the eye fundus with good accuracy.

It is another object of the invention to provided an improved ophthalmological measurement method and apparatus employing the laser speckle phenomenon which is simple and straightforward in construction and is able to measure the diameter of the blood vessel with good accuracy.

The invention provides an ophthalmological measurement method and apparatus in which the eye fundus is illuminated by a laser beam having a predetermined diameter and the motion of a laser speckle pattern formed by laser light scattered and reflected from the eye fundus is detected at an observation point as fluctuations in the speckle light intensity to produce a speckle signal which is evaluated for ophthalmological measurement. In this arrangement the speckle signal is evaluated in terms of a rate of change to discriminate edges of a blood vessel. The speckle signal is preferably integrated to produce an integrated speckle signal, which is analyzed in terms of the change rate, and a point at which the change rate becomes zero or approaches to zero is determined as an edge of the blood vessel to identify the blood vessel part in the eye fundus.

Any movement of the identified blood vessel part of the eye fundus is detected, and the position of the region illuminated by the laser beam and the position of the observation point are adjusted by an amount corresponding to the amount of blood vessel movement to track the blood vessel part automatically. Furthermore, both the edges of the identified blood vessel are used to determine the diameter thereof.

In such an arrangement, the laser beam of predetermined diameter is projected into the eye fundus by a laser beam projector and the movement of a speckle pattern formed by diffused light scattered by blood cells within the eye tissue passes through a light receiving system and is detected by a photosensor as fluctuations in speckle light intensity. The speckle signal mirrors the travel speed of the blood cells in the eye tissues. The size of speckles on the photosensor and the scanning speed of the photosensor are optimally set. The speckle light intensity will fluctuate more rapidly when cell velocities are high, and the averaging effect of the photosensor's storage time will result in a smaller output. Conversely, a low cell travel speed will decrease the lowering of the output from the photosensor. The speckle light intensity is sequentially read out from the photosensor and integrated to produce an integrated speckle signal having a less-inclined portion representative of a blood vessel part in the eye fundus. To locate an edge of the blood vessel, the integrated speckle signal is analyzed in terms of a rate of change, and a point at which the change rate becomes zero or approaches to zero is determined as an edge of the blood vessel to identify the blood vessel part in the eye fundus.

Movable mirrors are driven by an amount corresponding to shifts in the position of the blood vessel caused, for example, by eye movement, so that the position of the region illuminated by the laser beam and the observation position are controlled to automatically track the blood vessel. Furthermore, both the edges of the identified blood vessel are used to determine the diameter of the blood vessel. Thus, the invention provides an improved ophthalmological measurement method and apparatus which is able to detect eye movement and automatically track the movement in the eye fundus or measure the diameter of the blood vessel with a simplified structure and with good accuracy.

BRIEF DESCRIPTION OF THE DRAWINGS

The objects and features of the present invention will become more apparent from a consideration of the following detailed description taken in conjunction with the accompanying drawings in which:

FIG. 10 is a flow chart of the control process for tracking a blood vessel;

FIG. 11 is a flow chart of the control process for central position correction;

FIGS. 12a to 12f are diagrams showing the relationship between speckle size and CCD pixel size, and output signals;

FIGS. 13a and 13b are graphs showing speckle pattern travel speed and the waveform of a CCD output signal;

DETAILED DESCRIPTION OF THE PREFERRED EMBODIMENTS

Figure 1:
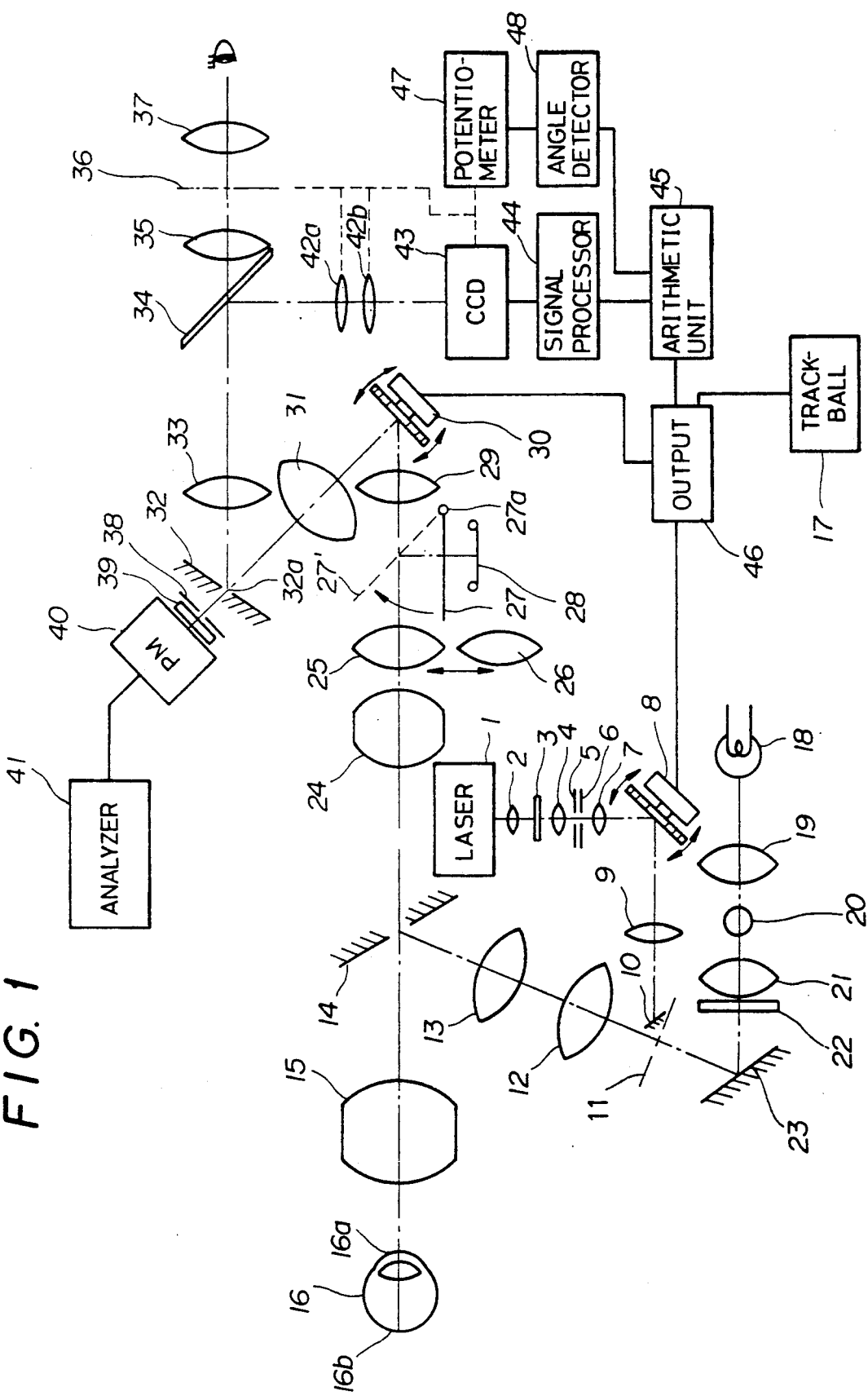
FIG. 1 is a diagram showing the structure of a first embodiment of an apparatus according to the present invention.

The invention will now be described in detail with reference to embodiments shown in the drawings.

The invention is particularly used for an ophthalmological measurement apparatus in which the eye fundus is illuminated by a laser beam having a prescribed diameter and the motion of a laser speckle pattern formed by laser light scattered and reflected from the eye fundus is detected at an observation point as fluctuations in the speckle light intensity to produce a speckle signal which is evaluated to measure a blood flow state in tissues in the eye fundus. Therefore, the embodiments described below are those which are applied to the ophthalmological measurement apparatus including a basic optical arrangement of an eye fundus camera to measure the blood flow state in the eye fundus tissue. The invention is, however, not limited to such embodiments but may be applied to another type of ophthalmological apparatus.

With reference to FIG. 1, a laser beam from a redlight He-Ne (wavelength: 632.8 nm) laser light source 1, for example, passes through a condenser lens 2 and a light quantity adjustment filter 3 for adjusting the beam intensity, and is then collimated by a collimator lens 4. Two apertures 5 and 6 are provided within the path of the beam for selectively adjusting the size and shape of the region of an eye fundus 16b of a subject's eye 16 being illuminated by the laser beam.

Figure 2:
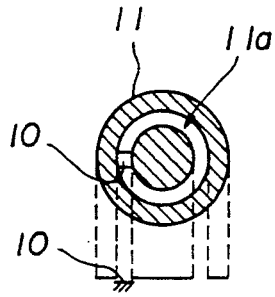
FIG. 2 is a diagram for explaining the structure of a ring slit.

The laser beam passes through a condenser lens 9 and is reflected by a mirror 10 provided in a transparent portion of an annular aperture 11a formed in a ring slit 11 arranged in an eye fundus camera illuminating projector, as shown in FIG. 2 (in which the non-transparent portion is indicated by shading). Such an arrangement enables the laser beam to be directed along the same optical path to the eye fundus as that followed by the beam of light projected into the eye fundus to provide illumination for photography and observation. The laser beam thus passes through relay lenses 12 and 13, is reflected by a ring mirror 14 and, via an objective lens 15, passes via the cornea 16a of the eye 16 under examination to the eye fundus 16b where the blood vessel of interest is irradiated with the laser beam for measurement and tracking.

A swingable mirror 8 is provided in the optical laser beam illumination system to deflect the laser beam spot in the eye fundus 16b. Prior to the start of measurement, this deflection is performed via an output section 46 using a means such as a trackball 17. The swingable mirror 8 can be controlled by an ordinary method such as a coagulator arrangement which allows independent control of the angle of mirror deflection in the x and y directions relative to the optical axis.

To minimize the discrepancy that has to be corrected arising from differences in laser beam deflection angles in the x and y directions, the angle at which the laser beam is reflected by the swingable mirror 8 is made as small as space will permit. The swingable mirror 8 is disposed at a position that is substantially a conjugate of the cornea 16a or pupil of the eye. This assures that the laser beam can be moved over the eye fundus without any major change in the position of beam incidence on the cornea.

The laser beam is provided on the same optical path as the photography and observation light beam. This arrangement is highly convenient since it enables the location within the eye fundus 16b at which the laser beam is being projected by the swingable mirror 8 to be brought within the field of view for photography or observation by using mechanisms for swinging and tilting the eye fundus camera vertically and horizontally and the eye fixation means.

This measurement and tracking region is also illuminated by an illuminating projector of the fundus camera to facilitate observation. The system for providing the illumination for observation is constituted of an observation light source 18, a condenser lens 19, a condenser lens 21, a filter 22 and a mirror 23 disposed on the same light path as a photographic light source 20.

Figure 3:
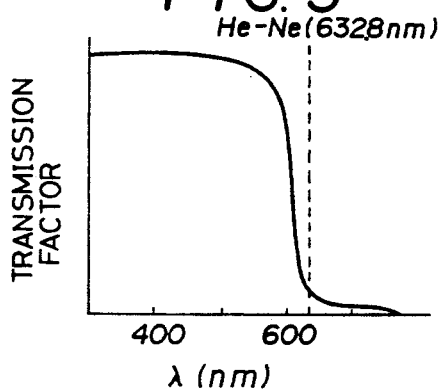
FIG. 3 is a characteristic curve showing the characteristics of a filter.

The filter 22 disposed between the condenser lens 21 and the mirror 23 is a wavelength separation filter having the type of characteristics shown in FIG. 3 to filter out red components from the observation and photographic light. A filter is selected that has spectral characteristics appropriate to the wavelength of the laser beam source that is employed.

Speckle light produced by the scattering of the laser beam in the eye fundus and reflected observation and photographic light passes through the objective lens 15, the ring mirror 14, a focusing lens 24, an imaging lens 25 or 26 and a relay lens 29, is reflected by a movable mirror 30 and passes through a relay lens 31 and is thereby formed into an image at a ring mirror 32. The light reflected by the ring mirror 32 passes through a relay lens 33 and is divided by a wavelength separation mirror 34. Cylindrical imaging lenses 42a and 42b form speckle light reflected by the wavelength separation mirror 34 into an image on a scanning type sensor CCD 43. The wavelength separation mirror 34 is set at an angle of about 45 degrees relative to the optical axis, and as the wavelength separation mirror 34 has the same kind of spectral characteristics as wavelength separation filter 22, shown in FIG. 3, it reflects most of the speckle light produced by the red He-Ne laser beam.

Light that is transmitted by the wavelength separation mirror 34 passes through an imaging lens 35 and forms an image at a reticle 36. The examiner can view this image through an eyepiece 37. The eyepiece 37 can be adjusted to compensate for individual differences in visual acuity; the reticle 36 is used as a reference for such adjustments.

Figure 4:
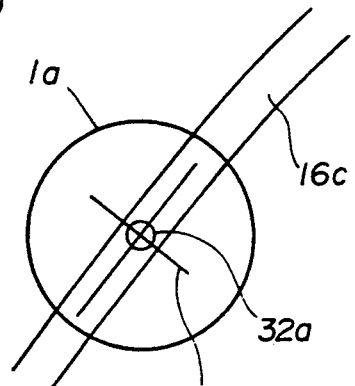
FIGS. 4 and 5 show observed images of the eye fundus.
Figure 5:
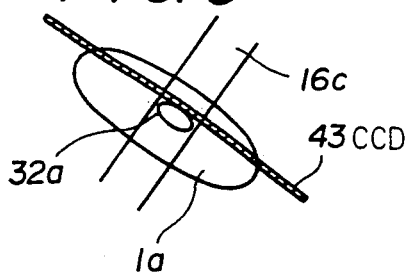

With reference to FIG. 4, the lines of the reticle 36 which intersect at right-angles can be differentiated, and the intersecting portion coincides with the center of an aperture 32a in the ring mirror 32. The reticle 36 can be rotated about the intersecting portion. Rotation of the reticle 36 to align it with a blood vessel 16c, as shown in FIG. 4, produces a synchronous rotation of the cylindrical imaging lenses 42a and 42b and the CCD 43, automatically orienting the CCD 43 perpendicularly to the image of the blood vessel. FIG. 5 illustrates the eye fundus image that will thus be formed on the face of the CCD 43. In the drawing, 1a denotes the area illuminated by the laser beam.

In view of factors relating to the diameter of speckles, the boiling motion of the speckle pattern and the sensitivity of the CCD 43, the cylindrical imaging lenses 42a and 42b are set so that the image of the eye fundus is formed on the CCD 43 with a lower magnification when it is in a direction parallel to the blood vessel 16c than when it is orthogonal to the blood vessel. As shown in FIG. 5, CCD 43 is provided at a position at which the image of the aperture 32a of the ring mirror 32 does not cross the face of the CCD 43, and the CCD 43 is arranged perpendicularly to the blood vessel 16c of interest.

For photography purposes a swingable mirror 27 is pivoted about a point 27a in the direction indicated by the arrow to raise it to a position 27', whereby the observation and photographic light including speckle light from the eye fundus is reflected by the swingable mirror 27 and forms an image which is photographed on photographic film 28. Thus, the system can be used for observation and photography of the eye fundus like an ordinary fundus camera. The ability to observe and photograph the eye fundus when it is being illuminated by the laser beam is desirable, as it enables the point of measurement to be directly confirmed and filmed.

In a system for receiving speckle light from the eye fundus and reflected light for observation and photography, light passing through the aperture 32a of the ring mirror 32 forms an image of the eye fundus 16b at a pinhole aperture 38. The light from the pinhole aperture 38 passes through an interference filter 39 and, when measurement is started, is received by a photomultiplier 40 which outputs a speckle signal to an analysis section 41. The interference filter 39 blocks light having a wavelength other than the 632.8 nm red light produced by the He-Ne laser.

The swingable mirror 30 is provided in the system for receiving speckle light from the eye fundus and light for observation and photography for positional correction purposes so that the image of the blood vessel in the eye fundus 16b is formed at the pinhole aperture 38 after passing through the ring mirror 32. Prior to the start of measurement, this adjustment is effected via the output section 46 using a means such as a trackball 17.

As described above, the trackball 17 is also used for operating the swingable mirror 8 prior to the measurement. A switch or other such means may be provided to switch trackball control between the swingable mirror 8 and the swingable mirror 30. The swingable mirror 30 can be controlled by any ordinary means which allows independent control of the angle of mirror deflection in the x and y directions relative to the optical axis. This applies also to the swingable mirror 8.

To minimize the discrepancy that has to be corrected arising from differences in laser beam deflection angles in the x and y directions, the angle at which the laser beam is reflected by the swingable mirror 30 is made as small as space will permit.

By locating the swingable mirror 30 at a position that is substantially a conjugate of the cornea 16a or pupil of the eye, the mirror 30 can be deflected to move the eye fundus 16b image at the pinhole aperture 38 without the beam being blocked by the pupil or other portion of the eye.

In the light receiving system, the imaging lens 25 is a wide angle type, wide enough to provide a view which allows all of the image of the eye fundus 16b to be checked. The imaging lens 26 is a narrow angle type with a high magnification factor which provides a magnified image to make it easy that the blood vessel image in the area illuminated by the laser beam is aligned with the pinhole aperture 38.

The imaging lenses 25 and 26 are arranged so that they can be switched instantaneously without moving the optical axis. This variable power lens arrangement facilitates accurate beam alignment with the required measurement position.

The diameter of the ring mirror 32 is just large enough to allow the passage of the light beam from the blood vessel 16c of interest, and the ring mirror 32 is located at a position that is substantially a conjugate of the eye fundus 16b. This assures that the examiner can align the system accurately by manipulating the image of the blood vessel of interest so that the image overlays the aperture of the ring mirror 32. FIG. 4 shows the image that this will produce. As the wavelength separation mirror 34 passes a small amount of speckle light, it is possible for the examiner to confirm the position of the illuminated area 1a.

When measurement is started, speckle light is received by the CCD 43 which outputs a signal to a signal processor 44. The signal processor 44 produces a blood vessel discrimination signal which is converted to a digital signal and output from the signal processor. If the blood vessel has moved owing to movement of the eyeball, for example, the amount of this movement is detected from the digital blood vessel discrimination signal by an arithmetic unit 45 which computes a correction amount by which the blood vessel as detected is to be moved back to an initial position. The computation result is output to the output section 46 which uses feedback correction to control the swingable mirror 30 and swingable mirror 8 so that the image of the eye fundus is constantly maintained at the same position at the pinhole aperture 38 and the laser beam continues to illuminate the same region in the eye fundus 16b.

The arithmetic unit 45 further serves to distinguish the blood vessel parts on the basis of the blood vessel discrimination signal and to calculate the blood vessel diameter. After calculation the results are output to the output section 46, which then displays the blood vessel diameter on a display.

Observation and photography light (other than red component light) together with the small amount of speckle light is transmitted by the wavelength separation mirror 34 and forms an image of the eye fundus at the reticle 36 also during the measurement process, and can therefore be observed by the examiner. The ability to thus observe the eye fundus during blood flow measurement is highly effective for preventing errors, as it enables any deviation from the area of interest to be observed.

Figure 6:
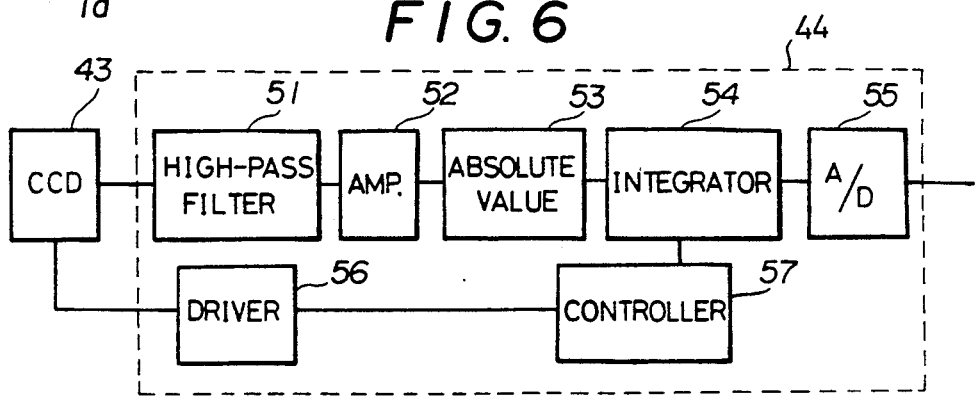
FIG. 6 is a block diagram of a signal processor used in the embodiment.

The electrical system from the signal processor 44 onwards will now be described. FIG. 6 is a schematic diagram of the signal processor. With reference to the drawing, the signal processor 44 is constituted of a drive circuit 56, a high-pass filter 51, an amplifier 52, an absolute value circuit 53, an integrator 54, an A/D converter 55 and a controller 57. Drive pulses generated by the drive circuit 56 are input to a 1,024-pixel linear CCD 43. The CCD 43 converts the speckle light to obtain a speckle signal which is passed through the high-pass filter 51 to extract just the high frequency components. This high frequency component signal is then amplified by the amplifier 52 and passed through the absolute value circuit 53 to obtain an absolute value.

Figure 7:
FIG. 7 shows the waveform of the signal output of an absolute value circuit.
Figure 8A:
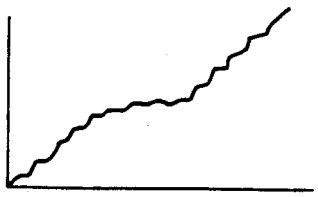
FIGS. 8a and 8b are the waveform of the signal output showing a signal processing for determining blood vessel edges.

The output signal thus obtained from the absolute value circuit 53 is illustrated in FIG. 7. The signal waveform shown is only that obtained from the central area of the CCD, not the whole; this also applies to FIGS. 12 and 13. The signal having the absolute value is then input to the integrator 54. The signal from the integrator is shown in FIG. 8a. The integrated signal is converted into an 8-bit digital signal by the A/D converter 55 and applied to the arithmetic unit 45.

Figure 8B:
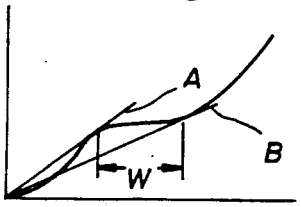

The signal obtained from the signal processor 44 and input to teh arithmetic unit includes noise as shown in FIG. 8a. The signal is therefore subjected to a smoothing process to obtain a smoothed signal as shown in FIG. 8b, in which a central less-inclined portion W indicates a blood vessel part. To obtain the blood vessel edges, therefore, tangential lines A and B are drawn from the origin to locate tangent points showing the blood vessel edges.

Figure 9A:
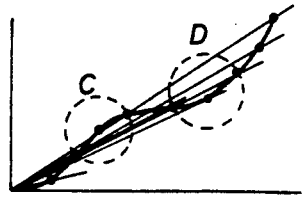
FIGS. 9a and 9b are the waveform of the signal output showing a signal processing for determining blood vessel edges.
Figure 9B:
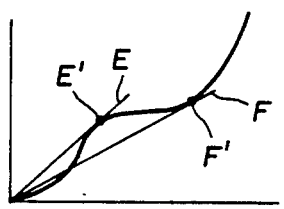

Thus, it will be proposed that the change rate (inclination) for lines between the origin and n points is obtained to locate, as shown in FIG. 9a, a point C having a transition of the change rate from increase to decrease and a point D having a transition from decrease to increase. For points within a range between C plus minus and D plus minus, the rate of change as seen from the origin is successively obtained to locate a point at which a difference of the change rate between the adjacent points becomes zero or approaches to zero. The thus located points are connected with the origin, as shown in FIG. 9b, to produce tangential lines E and F with tangential points E' and F', which are identified as both edges of the blood vessel.

The diameter of the thus identified blood vessel can be determined by multiplying the measured width between both edges of the blood vessel with a coefficient determined by the light receiving system. It is preferable to obtain the width of the identified blood vessel several times and to derive therefrom an average value or the smallest of the measured widths of the blood vessel for improvement in determining the blood vessel diameter.

A plurality of positional information is required if the amount by which the blood vessel has shifted is to be obtained just on the basis of blood vessel edge information. Also, this information will be affected to some extent by speckles. It is therefore necessary to obtain information from at least three edge searches in order to determine the movement of the blood vessel. By comparing the difference between the (m)th and (m+1)th data with the difference between the (m+1)th and (m+2)th data, it becomes possible to check whether or not there has been movement of the blood vessel in the period from the acquisition of the (m)th data to the (m+2)th data. If it is determined that there has been movement, it is possible to determine the amount of movement by, for example, obtaining the weighted averages of the differences, but in line with the approach summed up as "Don't correct if there has been no movement," the method shall now be explained which consists of taking the smallest of the differences as the amount of movement.

FIG. 10 is a flow chart of a process for determining the amount of blood vessel movement in accordance with this method. In step T1 the data up to the preceding two searches is stored prior to the data being updated. Step T2 is a blood vessel search. In this step, fresh blood vessel edge data is incorporated. In step T3 it is determined whether or not sufficient data has been prepared to enable the amount of movement to be obtained. If there is not enough data, the process returns to step T1; if the data is sufficient, the process advances to step T4. In step T4 differences C1, C2, D1, D2 between consecutive data sets are obtained for both edges, and in step T5 the presence or absence of movement is determined by determining whether or not the differences C1, C2, D1, D2 have the same sign, which is to say, whether or not the movement has been in the same direction in each case.

If the signs are the same and it is determined that movement has taken place in the same direction in each case, the process advances to step T6. If the signs are different and it is therefore determined that movement has not taken place in the same direction, the process moves to step T7. In step T6 the minimum value among C1, C2, D1, D2 is taken as the amount of movement, and after computing the amount of correction, taking into consideration the magnification and other such optical system factors, the necessary correction amount for returning the blood vessel to the initial position is obtained and output.

Step T7 is for when the movement of the blood vessel is so small that it is not detected from just one or two searches. In such a case, in step T7 the discrepancies C02, C01, C00, D02, D01, D00 between the initial positions (a0, b0) and each edge $(a_m, b_m)$, $(a_{m-1}, b_{m-1})$, $(a_{m-2}, b_{m-2})$ are obtained. The signs of C02, C01, C00, D02, D01, D00 are determined in step T8. The signs all being the same will signify that there has already been a shift to one side from the initial position, and the process advances to step T9, while if there are differences among the signs it will be unclear whether or not movement has taken place to one side from the initial position, so the process will return to step T1. In step T9 the minimum of the discrepancy values C02, C01, C00, D02, D01, D00 is taken as the amount of deviation and a correction amount is obtained and output.

In the output section 46 a pulse motor is driven by an amount that is in accordance with the correction amount output by the arithmetic unit 45, controlling the swingable mirrors 8 and 30 linked to the pulse motor. For automatic tracking, the swingable mirror 8 is driven to move the laser beam to the center of the blood vessel concerned. Likewise, the swingable mirror 30 is driven to implement automatic tracking by moving the speckle pattern observation point to the center of the blood vessel concerned.

When information is being obtained from a blood vessel in the eye fundus, in some cases there will be differences between measured values obtained from the center and the edges of a blood vessel. Central position correction is used to eliminate variance caused by such a difference.

FIG. 11 is a flow chart illustrating the central position correction procedure. Step R1 is for detecting the position of the blood vessel, and in step R2 the position of the blood vessel is detected continuously until the examination is begun. In step R3 the central position of the blood vessel is obtained from the most recent blood vessel position information immediately following the start of examination, the degree of discrepancy between this position and the central position of the CCD 43 is obtained and a correction is applied to eliminate any positional discrepancy between the blood vessel center and the CCD center. In step R4 the initial position of the blood vessel is set so that the blood vessel center coincides with the CCD center. In accordance with the initial position set in step R4, in step R5 positional correction is applied constantly to ensure that the center of the blood vessel coincides with the central position of the CCD 43, and this continues until examination is terminated in step R6. With this method, even if the system alignment by the examiner is off-center of the blood vessel, it will still be possible to examine the blood vessel center immediately following the start of the examination.

As described above, as the system is arranged so that when the reticle 36 is rotated relative to the optical axis the CCD 43 also rotates relative to the optical axis, the CCD can be set perpendicularly to the blood vessel. A potentiometer 47 is provided for detecting the angle of rotation of the CCD. An angle detection section 48 applies 8-bit A/D conversion to the output of the potentiometer 47 to obtain angle data, which is input to the arithmetic unit 45 to determine the rotation angle of the CCD. The arithmetic unit 45 calculates and outputs correction amounts to be applied in the x and y directions to correct for movement of the blood vessel.

It will not be possible to obtain a good speckle signal if there is a large discrepancy between the size of speckle images on the CCD 43 and the size of the CCD's pixels. As shown in FIG. 12a, speckles 93' which are larger than one of the pixels G of the CCD 43 will reduce the amount of incident light on the pixels, making it impossible to obtain a sufficiently strong speckle signal. FIG. 12b shows the type of speckle signal 93a that will result in such a case. On the other hand, if the speckles 93' are small compared to the pixels G of the CCD 43, as shown in FIG. 12e, the amount of incident light on the pixels will be averaged out, producing the kind of speckle signal 93a shown in FIG. 12f which lacks contrast. Speckles which are more or less the same size as the pixels as shown in FIG. 12c will produce a good speckle signal such as the signal 93a shown in FIG. 12d.

A method of using speckle signals as a basis for discriminating objects traveling at different speeds will now be described. Speckles which have a boiling motion require a complex explanation, so for the sake of simplicity the method will be explained in terms of translational motion. The left half of FIG. 13a depicts blood cells in tissues in the vicinity a of blood vessel which have a low travel speed, so the speckles 93' also show a low travel speed. The right half of the drawing depicts blood cells with a high travel speed such as the blood cells in a blood vessel, and which therefore give rise to speckles with a high travel speed. FIG. 13b shows the waveform of the corresponding signals output by a photosensor (i.e. a CCD). If the speed of the speckle pattern is higher than the scanning speed of a scanning sensor, large numbers of dark and light parts of speckles 93' will pass through the light receiving part of the CCD 43, giving rise to an output in which the light and dark portions are averaged and there is little difference between signals generated at different light receiving points.

On the other hand, if the speed of the speckle pattern is lower than the scanning speed of the scanning sensor, the number of dark and light parts of the speckles 93' passing through the light receiving part of the CCD 43 will decrease, so a strong signal will be output from a point on the light receiving part of the CCD 43 through which more light speckle portions pass, and a weak signal will be output from a point through which more dark speckle portions pass. Therefore, by optimizing the scanning speed of the scanning sensor with respect to speckle patterns arising from objects moving at different speeds and obtaining the intensity ratio of signals output by the scanning sensor, it becomes possible to discriminate between objects traveling at different speeds.

If, as shown in FIG. 5, with respect to the blood vessel image formed on the CCD 43, the ratio between the image in a direction parallel to the blood vessel 16c and the image in a direction perpendicular to the blood vessel is altered to compress it in the direction parallel to the blood vessel, this enables the amount of incident light on the CCD 43 to be increased without degradation of resolution in the direction perpendicular to the blood vessel. There will be a slight degradation in the signal intensity ratio of the light and dark speckle portions, but as there will be a considerable decrease in the dark portions, there will be few discrimination errors.

FIGS. 14 to 18 relate to other embodiments which have the same object as the embodiment described above but are not based on the optical system of a fundus camera. In the descriptions, parts that are the same as parts in the above embodiment have been given the same reference numerals, and a detailed description of such parts is omitted.

Figure 15:
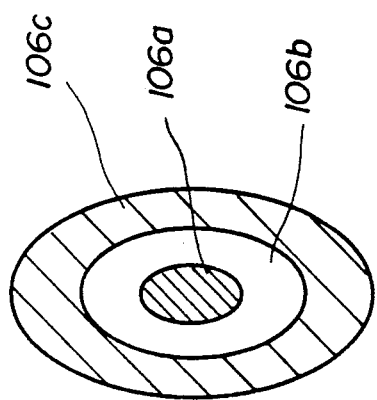
FIG. 15 shows details of a movable mirror.
Figure 14:
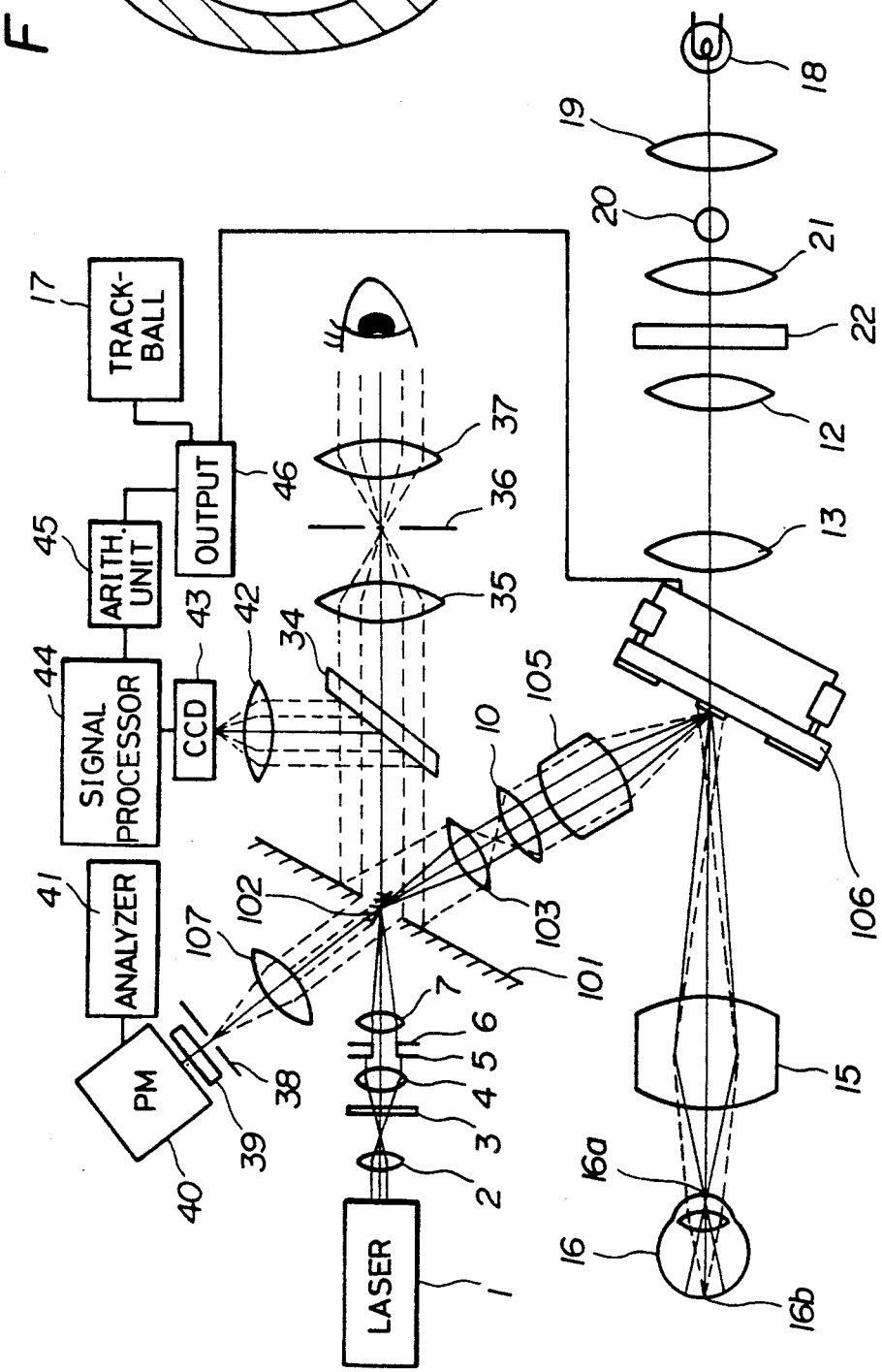
FIG. 14 is a schematic view of another embodiment of the apparatus of the invention.

With reference to FIG. 14, a laser beam is converged on a small mirror 102 located at a position that is a conjugate of the cornea 16a. The light passes through relay lenses 103 and 104 and a focusing lens 105, is reflected by a swingable mirror 106 located at a position that is a conjugate of the cornea 16a and is projected into the eye fundus 16b via the objective lens 15. As shown in FIG. 15, the swingable mirror 106 is constituted of a total reflection mirror 106a, a transparent section 106b and a portion 106c with a low reflectance that does not transmit light.

Part of the light which is scattered and reflected by the eye fundus 16b passes back along the same light path, is reflected by a ring mirror 101 and forms an image on the CCD 43. Light that is passed by the ring mirror 101 and the small mirror 102 is formed into an image at the pinhole aperture 38 by an imaging lens 107.

In the first embodiment the mirror used for beam alignment and tracking and the mirror used for observation-point alignment and tracking move independently, a drawback of which is that it complicates the alignment operation. In addition, during tracking the mirrors would sometimes move out of mutual alignment. To solve such problems, in this embodiment the function of the two mirrors have been integrated into a single mirror.

Figure 16:
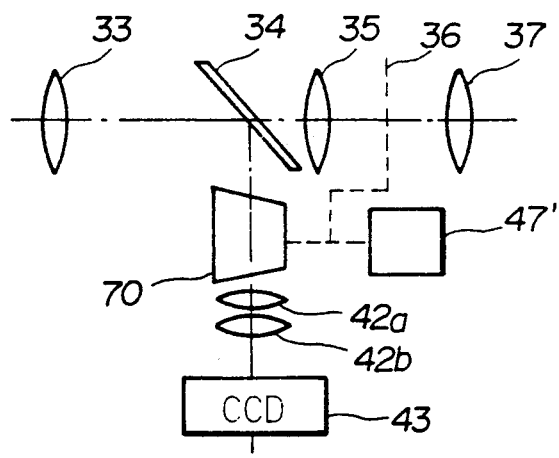
FIG. 16 shows the arrangement of an image rotator.

An image rotator 70 may be used to arrange the blood vessel image perpendicularly to the CCD 43. With reference to FIG. 16, the blood vessel image formed on the face of the CCD 43 may be rotated instead. The image rotator is linked to the reticle 36 so that both rotate together. For angular data a potentiometer 47' is provided for detecting the angle of rotation of the image rotator.

Figure 17:
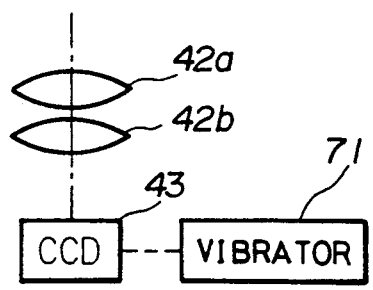
FIGS. 17 and 18 show an arrangement for oscillating an image on the CCD.
Figure 18:
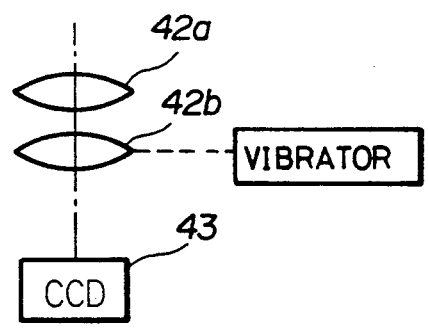

With reference to FIG. 17, the CCD 43 may be oscillated by a vibrator 71 at a low frequency and amplitude compared to the movement of speckles in the direction of the blood vessel the image of which is formed on the CCD. Alternatively, the vibrator 71 may be arranged so that it oscillates the lens 42b disposed in front of the CCD. Even with the use of oscillations having a low frequency and amplitude compared to the movement of speckles, the effect obtained will be the same as when the image is compressed in a direction parallel to the blood vessel.

When the CCD 43 is a linear sensor, no resolution is required in a direction parallel to the long axis of the blood vessel the image of which is produced by the laser speckle light. Therefore, the compression along the long axis of the blood vessel can be effected at the Fourier plane, but it must be effected at the image plane in the direction perpendicular to the blood vessel because it needs resolution.

While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiments disclosed as the best mode contemplated for carrying out the invention, but that the invention will include all embodiments falling within the scope of the appended claims.

What is claimed is:

1. An ophthalmological measurement method comprising the steps:
    projecting a laser beam having a predetermined diameter to an eye fundus;
    detecting motion of a laser speckle pattern formed by laser light scattered and reflected from the eye fundus at an observation point as fluctuations in the speckle light intensity;
    producing a speckle signal from the fluctuations in the speckle light intensity;
    evaluating the speckle signal in terms of a rate of change to discriminate edges of a blood vessel to identify a blood vessel part of the eye fundus;
    detecting any movement of the identified blood vessel part of th eye fundus; and adjusting the position of the region illuminated by the laser beam and the position of the observation point by an amount corresponding to the amount of blood vessel movement to track the blood vessel part automatically.

2. An ophthalmological measurement method according to claim 1, wherein the speckle signal is integrated to produce an integrated speckle signal, which is analyzed in terms of the change rate, and a point at which the change rate becomes zero or approaches to zero is determined as an edge of the blood vessel.

3. An ophthalmological measurement method according to claim 1, further comprising the steps of discriminating both edges of the blood vessel and determining the diameter thereof.

4. An ophthalmological measurement method according to claim 3 wherein the diameter of the blood vessel is determined by multiplying a measured distance between both the edges of the blood vessel with a predetermined coefficient.

5. An ophthalmological measurement method according to claim 1, wherein sets of data of the blood vessel edge are sampled, differences between consecutive sets of data are weighted to obtain the amount of movement of the blood vessel image, and correction amounts for the automatic tracking are obtained from the amount of movement.

6. An ophthalmological measurement method according to claim 1, wherein the automatic tracking is implemented by moving the blood vessel image to be tracked to the speckle pattern observation point.

7. An ophthalmological measurement method according to claim 1, wherein the position of the region illuminated by the laser beam automatically tracks the center of the blood vessel to be tracked.

8. An ophthalmological measurement apparatus in which an eye fundus is illuminated by a laser beam having a predetermined diameter and the motion of a laser speckle pattern formed by laser light scattered and reflected from the eye fundus is detected at an observation point as fluctuations in the speckle light intensity to produce a speckle signal which is evaluated for ophthalmological measurement, comprising:

an optical system for projecting the laser beam to a region of the eye fundus having a blood vessel to be examined;

means for detecting movement of a laser speckle pattern formed by light scattered by the eye fundus as fluctuations in the light intensity of the speckles at an observation point;

means for integrating a speckle signal obtained from the detecting means, the speckle signal being evaluated in terms of a rate of change to discriminate edges of the blood vessel to identify a blood vessel part of the eye fundus;

means for detecting the amount of any movement the blood vessel part makes; and means for automatically tracking the blood vessel part by adjusting the position of the region illuminated by the laser beam and the position of the observation point by an amount corresponding to the detected amount of blood vessel movement.

9. An ophthalmological measurement apparatus according to claim 8, further comprising means for determining the diameter of the blood vessel on the basis of the discriminated edges.

10. An ophthalmological measurement apparatus according to claim 8, further comprising a mechanism for deflecting the laser beam into alignment with the blood vessel to be tracked.

11. An ophthalmological measurement apparatus according to claim 10, wherein the mechanism moves the laser beam by deflecting a mirror.

12. An ophthalmological measurement apparatus according to claim 11, wherein the angle of reflection by the mirror is small enough to prevent overlapping of the beams.

13. An ophthalmological measurement apparatus according to claim 8, wherein a scanning sensor is provided at the observation point for detecting fluctuations in speckle light intensity.

14. An ophthalmological measurement apparatus according to claim 13, wherein the size of a unit receiving area of th scanning sensor is approximately the same as the size of the speckles.

15. An ophthalmological measurement apparatus according to claim 13, wherein the movement speed of the speckles is lower than the scanning speed of the scanning sensor.

16. An ophthalmological measurement apparatus according to claim 13, further comprising a plurality of scanning sensors and circuitry for selecting the output with the maximum value among the outputs of the sensors.

17. An ophthalmological measurement apparatus according to claim 8, further comprising a first mirror for deflecting the laser beam into the blood vessel for automatic tracking and a second mirror for deflecting the blood vessel image into alignment with the observation point.

18. An ophthalmological measurement apparatus according to claim 17, wherein both the mirrors are integrated.

* * * * *